United States Patent
Valerino, Sr.

(10) Patent No.: US 9,539,178 B1
(45) Date of Patent: Jan. 10, 2017

(54) MEDICAL OBJECT DISTRIBUTION SYSTEM AND METHOD

(71) Applicant: Fredrick M. Valerino, Sr., Timonium, MD (US)

(72) Inventor: Fredrick M. Valerino, Sr., Timonium, MD (US)

( * ) Notice: Subject to any disclaimer, the term of this patent is extended or adjusted under 35 U.S.C. 154(b) by 0 days.

(21) Appl. No.: 15/157,388

(22) Filed: May 17, 2016

Related U.S. Application Data

(63) Continuation-in-part of application No. 15/157,378, filed on May 17, 2016.

(51) Int. Cl.
  *B65G 51/34* (2006.01)
  *A61J 7/00* (2006.01)
  *B65G 51/02* (2006.01)
  *B65G 43/08* (2006.01)

(52) U.S. Cl.
  CPC .............. *A61J 7/0076* (2013.01); *B65G 43/08* (2013.01); *B65G 51/02* (2013.01); *B65G 2203/0216* (2013.01)

(58) Field of Classification Search
  CPC ......... B65G 43/08; B65G 51/34; B65G 51/36; A61J 2205/60; G06F 19/3462; E04F 17/12
  USPC .......... 406/2, 3, 12, 110, 176, 197; 700/225, 700/229, 230
  See application file for complete search history.

(56) References Cited

U.S. PATENT DOCUMENTS

| | | | |
|---|---|---|---|
| 2,679,990 A | 6/1954 | Mathzeit et al. | |
| 3,070,403 A | 12/1962 | Shelton | |
| 3,759,577 A | 9/1973 | Manzer | |
| 3,953,078 A | 4/1976 | Aitken | |
| 4,076,321 A | 2/1978 | Haight et al. | |
| 4,084,770 A | 4/1978 | Warmann | |
| 4,108,498 A | 8/1978 | Bentsen | |
| 4,157,796 A | 6/1979 | Warmann | |
| 4,210,801 A | 7/1980 | Gomez et al. | |
| 4,458,602 A * | 7/1984 | Vandersteel | B65G 51/04 104/138.1 |
| 4,820,086 A | 4/1989 | Kieronski | |
| 4,995,765 A | 2/1991 | Tokuhiro et al. | |
| 5,192,170 A | 3/1993 | Lang | |

(Continued)

OTHER PUBLICATIONS

EXAIR Corporation, Line Vac, 2014, available at www.exair.com.

*Primary Examiner* — Joseph Dillon, Jr.
(74) *Attorney, Agent, or Firm* — Hanna Bondarik Mosolygo

(57) ABSTRACT

Systems, methods, and modes for distribution of medical objects, such as medicines, from a sending station at a pharmacy or a nursing station to one of a plurality of receiving stations located by the patient's bedside via pneumatic tubing without a dedicated carrier. The system is a one-way system configured for allowing the medical object to travel in one direction from a sending station to one of the receiving stations. The pneumatic tube system comprises a sending station, a plurality of receiving stations routably connected to the sending station via the pneumatic tubing, a pump, and a system controller in signal communication with the sending station, the receiving station, and the pump. The system controller receives delivery information from the sending station, identifies an intended receiving station using the delivery information, and sends commands to the pneumatic tube system to control routing of the medical object from the sending station to the identified receiving station in the pneumatic tubing.

31 Claims, 5 Drawing Sheets

(56) References Cited

U.S. PATENT DOCUMENTS

| | | |
|---|---|---|
| 5,217,328 A | 6/1993 | Lang |
| 5,234,292 A | 8/1993 | Lang |
| 5,354,000 A | 10/1994 | Wright et al. |
| 5,385,105 A | 1/1995 | Withers, Jr. et al. |
| 5,402,938 A | 4/1995 | Sweeney |
| 5,636,947 A | 6/1997 | Valerino, Sr. et al. |
| 5,712,789 A | 1/1998 | Radican |
| 5,805,454 A | 9/1998 | Valerino, Sr. et al. |
| 5,864,485 A | 1/1999 | Hawthorne et al. |
| 5,896,297 A | 4/1999 | Valerino, Sr. |
| 6,048,086 A | 4/2000 | Valerino, Sr. |
| 6,173,212 B1 | 1/2001 | Valerino, Sr. |
| 6,202,004 B1 | 3/2001 | Valerino, Sr. |
| 6,283,909 B1 | 9/2001 | Sharp |
| 6,477,442 B1 | 11/2002 | Valerino, Sr. |
| 6,561,691 B1 | 5/2003 | McCann et al. |
| 6,599,476 B1 | 7/2003 | Watson et al. |
| 6,637,587 B2 | 10/2003 | Britton |
| 6,702,150 B2 | 3/2004 | Sumetzberger |
| 6,712,561 B1 | 3/2004 | Valerino, Sr. et al. |
| 7,243,002 B1 | 7/2007 | Hoganson et al. |
| 7,326,005 B1 * | 2/2008 | Castro .................... B65G 51/22 406/19 |
| 7,328,084 B1 | 2/2008 | Hoganson et al. |
| 7,363,106 B1 | 4/2008 | Hoganson et al. |
| 7,424,340 B2 | 9/2008 | Owens |
| 8,113,349 B2 | 2/2012 | Sansoucy et al. |
| 8,116,906 B2 | 2/2012 | Valerino, Sr. |
| 8,153,001 B2 | 4/2012 | Peters |
| 8,268,179 B2 | 9/2012 | Peters |
| 8,371,773 B2 | 2/2013 | Bryan, Jr. et al. |
| 2005/0049746 A1 | 3/2005 | Rosenblum |
| 2008/0292414 A1 * | 11/2008 | Owens .................... B65G 51/32 406/182 |
| 2014/0270995 A1 * | 9/2014 | Hoganson .............. B65G 51/26 406/110 |
| 2015/0025675 A1 | 1/2015 | Valerino, Sr. |
| 2015/0274441 A1 * | 10/2015 | Jones .................... B65G 51/32 700/230 |
| 2015/0298919 A1 * | 10/2015 | Le .......................... B65G 51/24 406/110 |

* cited by examiner

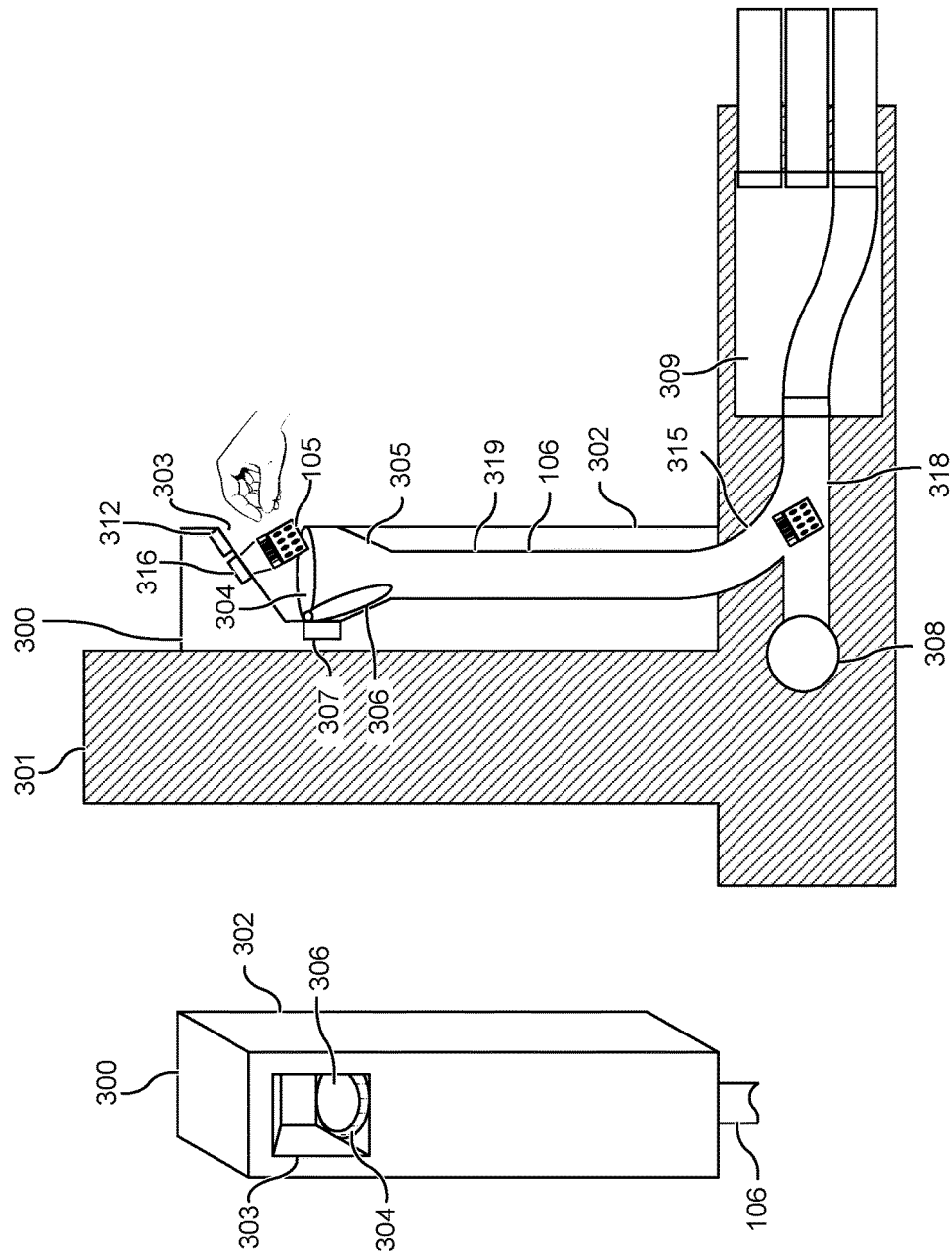

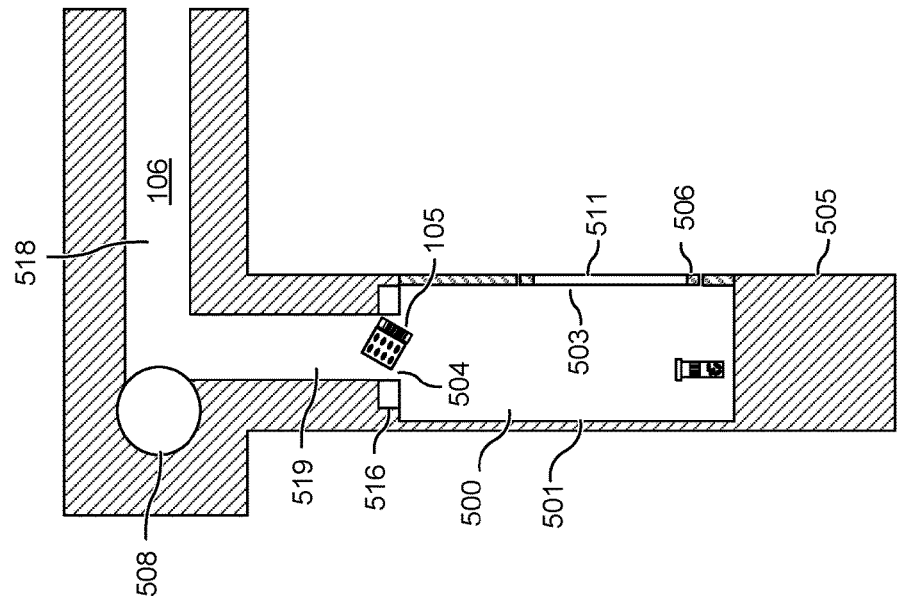
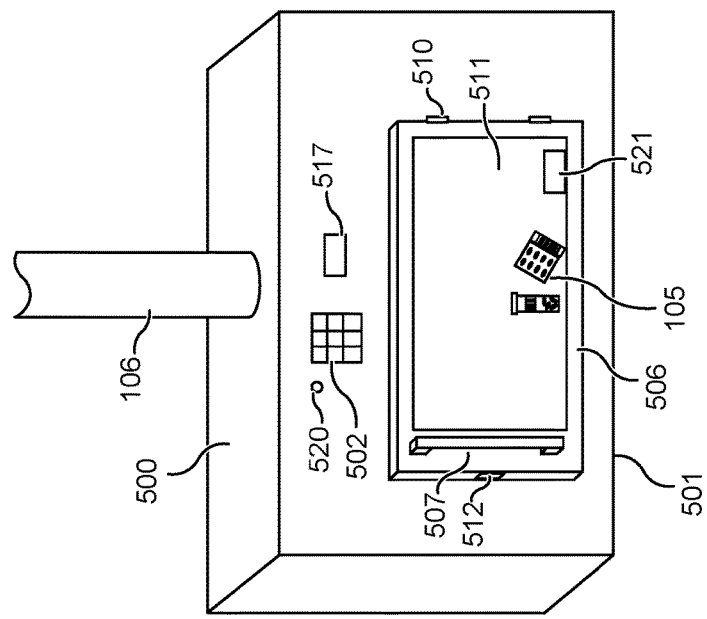
FIG. 5B
FIG. 5A

MEDICAL OBJECT DISTRIBUTION SYSTEM AND METHOD

BACKGROUND OF THE INVENTION

Technical Field

Aspects of the embodiments relate to distribution of medical objects, such as medicines, and more specifically to systems, methods, and modes for distribution of medical objects from a pharmacy or a nursing station to the patient's bedside via pneumatic tubing.

Background Art

The practice of dispensing and delivery of drugs at medical institutions, such as hospitals, is a time consuming process. Medications need to be prepared and transported in a secure environment while ensuring the safety of patients and hospital workers. Typically, in a hospital environment a prescription is written by a medical practitioner that requests the pharmacy to provide a medical object to a patient. Such medical object may include medicine, such as oral, topical, or suppository pharmaceutical drugs, small medical supplies or devices, such as sterile items, thermometers, bandages, dressings, or the like, used to diagnose, cure, treat, or prevent disease. The prescription is filled by the pharmacy and delivered to a nursing station.

Pneumatic tube systems have been used in hospitals to transport medications from the pharmacy to the nursing station. Pneumatic delivery systems are used extensively for its rapid, efficient, and secure transportation of a wide variety of articles. Such pneumatic tube systems comprise a sending station located at the pharmacy in communication with a plurality of receiving stations located throughout the hospital. To transport an object via conventional pneumatic tubing, the object needs to be first placed within a carrier, which is transported via the pneumatic tubing to a destination by air under either positive or negative pressure created by a blower or a fan. The interior of the closed tube and the outer dimension of the carrier form a seal so that the carrier can be propelled between pneumatic stations. When the doctor prescribes medication, the pharmacy fills the prescription and delivers it inside the carrier to a desired receiving station via the pneumatic tube system.

The nurse at the receiving station must open the carrier and determine to which patient at which location (e.g., a patient room, emergency room (ER), operating room (OR), or phlebotomy room) the nurse needs to deliver the prescription. The medications are sorted at the nursing station for delivery to the patients by nurses responsible for the patient. In many instances, however, the medications get mixed up due to frequent handling by numerous personnel. Constantly opening and closing of carriers may be time consuming. Secure storage at the nursing station may not be available as the medications await delivery by the nurses. Nurses delivering the medications may pick up the wrong medication to deliver. User error may occur during the identification of the room and patient resulting in missdelivery of the prescription. Additionally, errors may occur as nurses may be delivering a plurality of medications to various rooms.

Accordingly, a need has arisen for systems, methods, and modes for quick and secure distribution of medical objects, such as medicines, from a pharmacy or a nursing station to the patient's bedside via pneumatic tubing that entails minimal amount of handling.

SUMMARY OF THE INVENTION

It is an object of the embodiments to substantially solve at least the problems and/or disadvantages discussed above, and to provide at least one or more of the advantages described below.

It is therefore a general aspect of the embodiments to provide systems, methods, and modes for quick and secure distribution of medical objects, such as medicines, from a pharmacy or a nursing station to the patient's bedside via pneumatic tubing that entails minimal amount of handling.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Further features and advantages of the aspects of the embodiments, as well as the structure and operation of the various embodiments, are described in detail below with reference to the accompanying drawings. It is noted that the aspects of the embodiments are not limited to the specific embodiments described herein. Such embodiments are presented herein for illustrative purposes only. Additional embodiments will be apparent to persons skilled in the relevant art(s) based on the teachings contained herein.

DISCLOSURE OF INVENTION

According to an embodiment, a pneumatic tube system is provided for distribution of medical objects in a medical environment without a dedicated carrier. The system is a one-way system configured for allowing the medical object to travel in one direction from a sending station to one of the receiving stations. The pneumatic tube system comprises a sending station, a plurality of receiving stations routably connected to the sending station via the pneumatic tubing, a pump, and a system controller in signal communication with the sending station, the receiving station, and the pump. The sending station comprises a housing having a first opening on its front face for receiving a medical object and a second opening in communication with pneumatic tubing for transporting the medical object from the sending station. The pump is configured for creating a pressure differentiation within the pneumatic tubing for transmitting the medical object from the sending station to one of the receiving stations. The system controller comprises a processor and a memory encoding one or more processor-executable instructions, which when executed by the processor, cause acts to be performed comprising: (i) receiving delivery information from the sending station; (ii) identifying an intended receiving station using the delivery information; and (iii) sending commands to the pneumatic tube system to control routing of the medical object from the sending station to the identified receiving station in the pneumatic tubing. The system may further comprise a diverter having a plurality of outlet ports each in communication with a selected receiving station via pneumatic tubing, wherein the diverter is controlled by the system controller to divert the medical object to an outlet port in communication with the identified receiving station.

According to an embodiment, the second opening in the sending station comprises a funnel portion that tapers from a wide end to a narrow end, wherein the wide end is in communication with the first opening and wherein the narrow end is in communication with a terminal end of the pneumatic tubing. The funnel portion is configured for guiding the medical object into the pneumatic tubing. Either the first opening or the second opening may comprise a door to restrict access to the sending station. The second opening may comprise a valve configured for releasing pressure created by the pump such that the user can maintain the door opened. The sending station may comprise a door open sensor configured for sensing that the door has been opened, wherein the door open sensor is configured for triggering activation of the pump. The sending station may further comprise a proximity or motion sensor configured for detecting the proximity of a user to trigger at least one of opening of the door and activation of the pump. The door may comprise a lock and the sending station may comprise a user interface for receiving user identification information to authenticate the user and unlock the door upon successful authentication. The sending station may further comprise a user interface configured for receiving the delivery information.

According to an embodiment, each receiving station may comprise a door to restrict access to the receiving station. The door may comprise a lock and the receiving station may comprise a user interface for receiving user identification information to authenticate the user and unlock the door upon successful authentication. Each receiving station may further comprise a proximity or motion sensor configured for detecting a received medical object within the receiving station, and the receiving station may comprise an indicator light that is activated upon a trigger by the proximity or motion sensor to indicate that the receiving station has received a delivery. A notification may also be sent to a handheld device of a user upon a trigger by the proximity or motion sensor to indicate that the receiving station has received the delivery.

According to an embodiment, the pneumatic tubing comprises a flexible reinforced hose. The hose may comprises material including, but not limited to plastic, polyvinyl chloride (PVC), polyethylene, polypropylene, rubber, silicone, metal, aluminum alloy, corrugated stainless steel alloy, reinforced or coated fabric, including polyester, nylon, or fiberglass, and any combinations thereof. The hose may comprise an inner diameter ranging from approximately one inch to approximately four inches in size.

According to an embodiment, the pump may create one of a positive pressure or a negative pressure within the pneumatic tubing. The pump may create pressure ranging from approximately four pounds to approximately six pounds of pressure. According to one embodiment, the pump may be located in proximity to the sending station and comprises a positive pressure air compressor. The second opening of the sending station may be connected to a substantially vertical portion of pneumatic tubing that is connected to a substantially horizontal portion of pneumatic tubing via a bend. The pump may be connected at the bend in a T configuration and aligned with the horizontal portion of pneumatic tubing. The medical object may be dropped via gravity along the vertical portion until reaching the bend and then travel along the horizontal portion via a positive pressure created by the pump. The horizontal portion of pneumatic tubing may be connected to a diverter configured for changing a pneumatic tubing path to route the medical object to the identified receiving station.

According to another embodiment, the may comprises a plurality of pumps each located in proximity to a respective receiving station and comprises a negative pressure air compressor. The receiving station may be connected to a substantially vertical portion of pneumatic tubing that is connected to a substantially horizontal portion of pneumatic tubing via a bend. The pump may be connected at the bend in a T configuration and aligned with the horizontal portion of pneumatic tubing. The medical object may travel along the horizontal portion via a negative pressure created by the pump until reaching the bend and then drop via gravity along the vertical portion into the receiving station. According to another embodiment, the pump comprises an in-line pump connected to a compressed air source configured for creating a positive pressure at an outlet of the in-line pump According to an embodiment, the sending station and/or the receiving station may comprise an identifying tag reader configured for reading an ID tag attached to the medical object. The identifying tag reader may read the ID tag attached to the medical object to obtain the delivery information used by system controller to identify the intended receiving station. The system controller may identify the intended receiving station by querying a patient file stored on a database with the delivery information, wherein the patient file may include information including, but not limited to a unique ID number associated with the medical object, a patient's unique ID, a name of the patient, room ID of the patient, bed ID of the patient, receiving station ID associated with the patient, one or more IDs of authorized users allowed access to the receiving station associated with the patient, name, strength, diluent, and dosage of the medical object and any combinations thereof. The identifying tag reader may be configured to read tags including, but not limited to an optically scannable identifier tag, a barcode, a radio-frequency identification (RFID) tag, a near field communication (NFC) tag, or any combinations thereof.

The system controller may capture tracking information associated with sending and receiving the medical object. Delivery data may be logged by the system controller in a database upon scanning the ID tag at the sending station. The delivery data may comprises at least one of an ID of the sending station, an ID of the sending user, information obtained from the ID tag, a time and date the medical object was sent by the sending station, and any combinations thereof. Reception data may be logged by the system controller in a database upon scanning the ID tag at the receiving station. The reception data may comprise at least one of an ID of the receiving station, information obtained from the ID tag, a time and date the medical object arrived at the receiving station, the time a door at the receiving station was unlocked and the medical object was retrieved from the receiving station, a receiving user ID, and any combinations thereof.

According to another embodiment a method is provided for distributing medical objects in a medical environment without a dedicated carrier from a sending station to one of a plurality of receiving stations each located in proximity of a patient bedside. The method comprises: (i) receiving delivery information from the sending station routably connected to the plurality of receiving stations via the pneumatic tubing; (ii) identifying an intended receiving station using the delivery; (iii) receiving a medical object via a first opening on a front face of a sending station and transporting the medical object from the sending station through a second opening in communication with pneumatic tubing; (iv) sending commands to the pneumatic tube system to control routing of the medical object from the sending station to an identified receiving station in the pneumatic tubing; and (v) creating a pressure differentiation via a pump within the pneumatic tubing for transmitting the medical object from the sending station to the identified receiving station.

BRIEF DESCRIPTION OF THE DRAWINGS

The above and other objects and features of the embodiments will become apparent and more readily appreciated from the following description of the embodiments with reference to the following figures. Different aspects of the embodiments are illustrated in reference figures of the drawings. It is intended that the embodiments and figures disclosed herein are to be considered to be illustrative rather than limiting. The components in the drawings are not necessarily drawn to scale, emphasis instead being placed upon clearly illustrating the principles of the aspects of the embodiments. In the drawings, like reference numerals designate corresponding parts throughout the several views.

BRIEF DESCRIPTION OF THE SEVERAL VIEWS OF THE DRAWING

Figure 1:
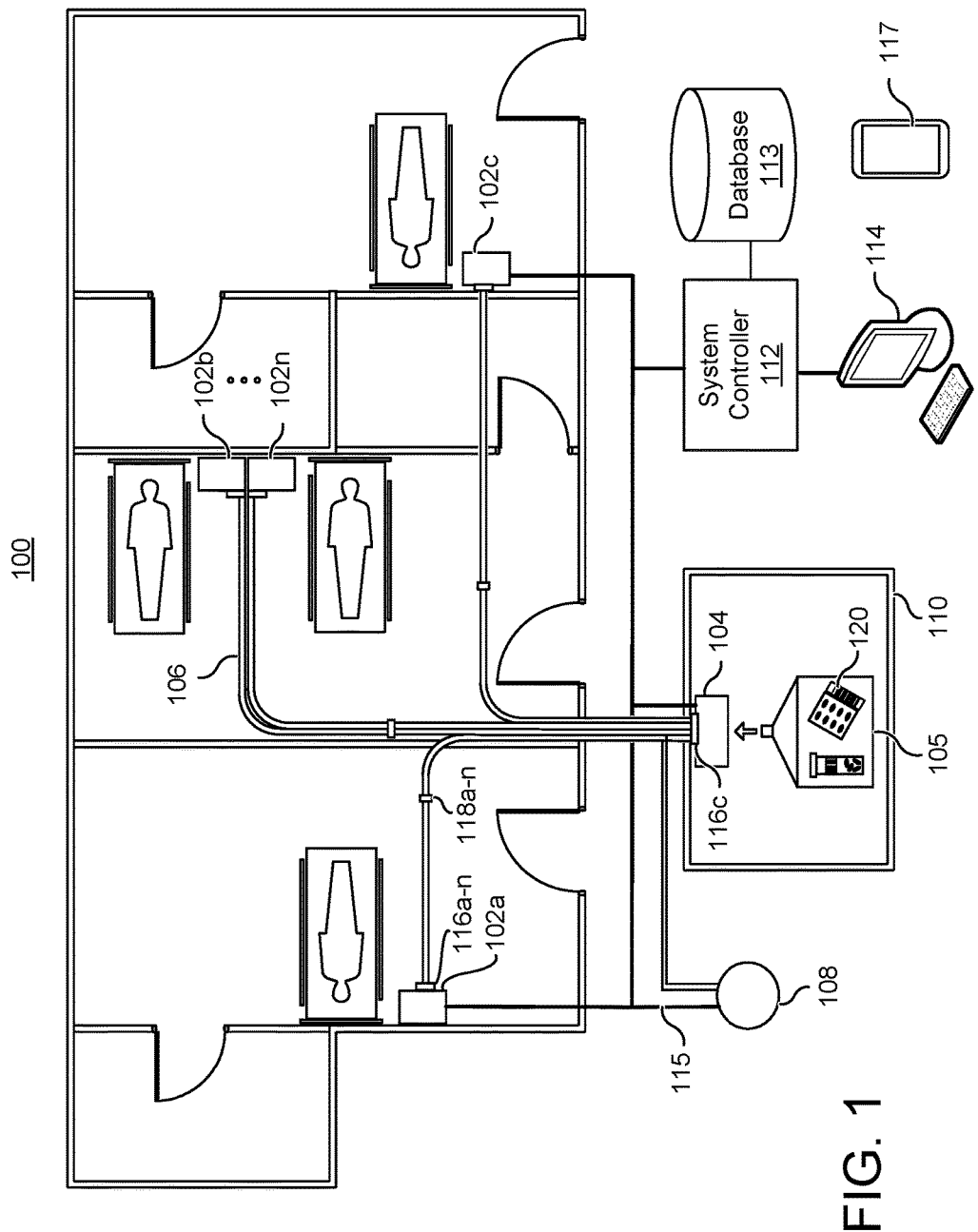
Figure 2A:
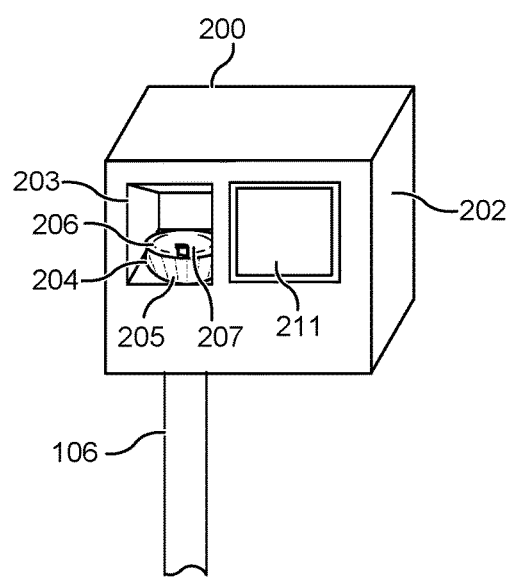
Figure 2B:
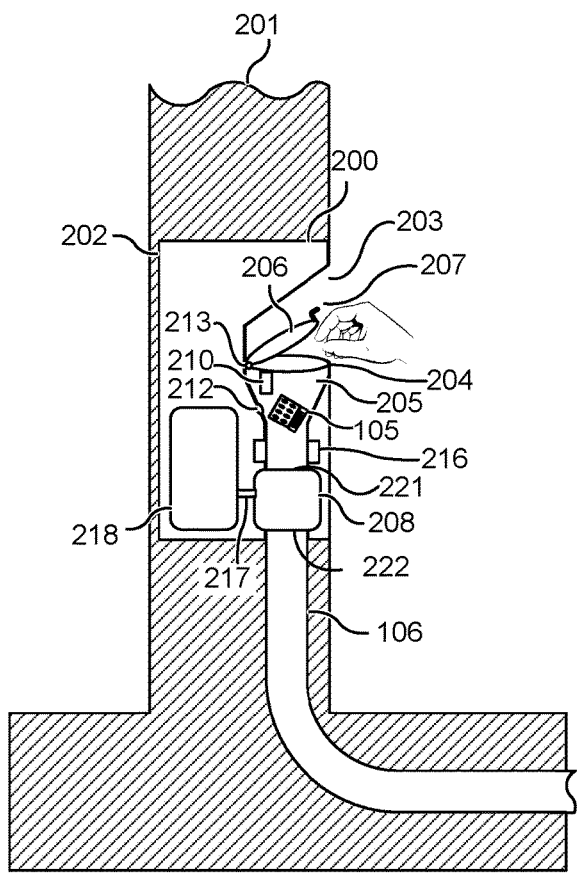
Figure 4A:
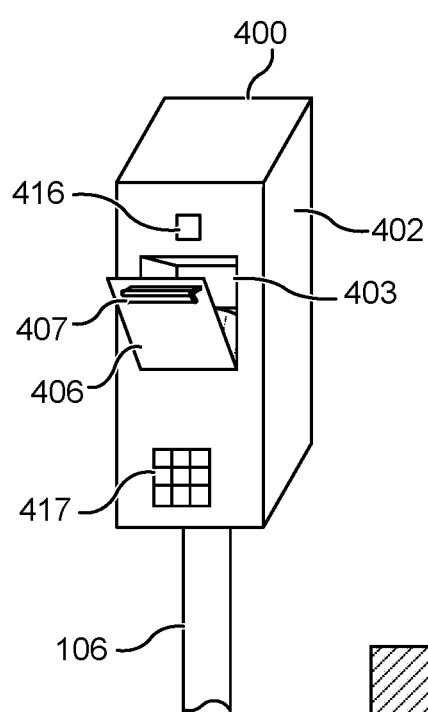
Figure 4B:
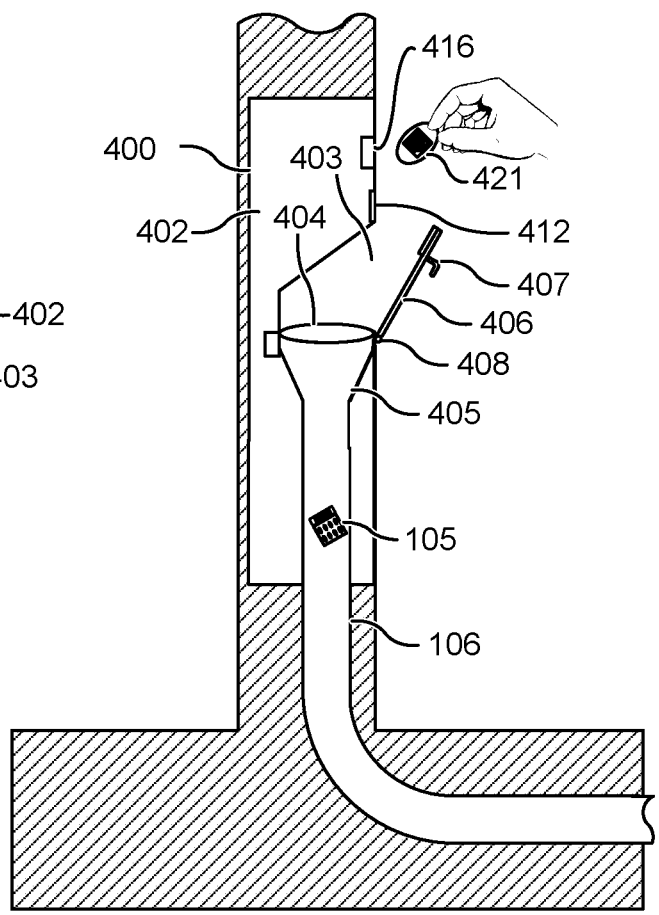

FIG. 1 illustrates a block diagram of a pneumatic system for distribution of medical objects according to an illustrative embodiment;

FIG. 2A illustrates a perspective view of a pneumatic sending station according to an illustrative embodiment;

FIG. 2B illustrates a partially cross-sectional side view of the pneumatic sending station in FIG. 2A according to an illustrative embodiment;

FIG. 3A illustrates a perspective view of a pneumatic sending station according to another illustrative embodiment;

FIG. 3B illustrates a partially cross-sectional side view of the pneumatic sending station in FIG. 3A according to an illustrative embodiment;

FIG. 4A illustrates a perspective view of a pneumatic sending station according to another illustrative embodiment;

FIG. 4B illustrates a partially cross-sectional side view of the pneumatic sending station in FIG. 4A according to an illustrative embodiment;

FIG. 5A illustrates a perspective view of a receiving station according to an illustrative embodiment; and FIG. 5B illustrates a partially cross-sectional side view of the pneumatic receiving station in FIG. 5A according to an illustrative embodiment.

DETAILED DESCRIPTION OF THE INVENTION

The embodiments are described more fully hereinafter with reference to the accompanying drawings, in which embodiments of the inventive concept are shown. In the drawings, the size and relative sizes of layers and regions may be exaggerated for clarity. Like numbers refer to like elements throughout. The embodiments may, however, be embodied in many different forms and should not be construed as limited to the embodiments set forth herein. Rather, these embodiments are provided so that this disclosure will be thorough and complete, and will fully convey the scope of the inventive concept to those skilled in the art. The scope of the embodiments is therefore defined by the appended claims.

Reference throughout the specification to "one embodiment" or "an embodiment" means that a particular feature, structure, or characteristic described in connection with an embodiment is included in at least one embodiment of the embodiments. Thus, the appearance of the phrases "in one embodiment" on "in an embodiment" in various places throughout the specification is not necessarily referring to the same embodiment. Further, the particular feature, structures, or characteristics may be combined in any suitable manner in one or more embodiments.

The different aspects of the embodiments described herein pertain to the context of systems, methods, and modes for distribution of medical objects, such as medicines, from a pharmacy or a nursing station to the patient's bedside via pneumatic tubing, but is not limited thereto, except as may be set forth expressly in the appended claims. While the present principles are described with respect to distribution of medical objects at a hospital, the present principles may also be used in, but are not limited to, other medical or industrial facilities, physician offices, managed care facilities, nursing homes, long term care, rest areas, pharmacies, blood test centers, laboratories, such as clinical laboratories, biotechnology or pharmaceutical manufacturers' facilities, or other facilities where medical object distribution is desired.

Referring to FIG. 1, there is shown a diagram illustrating a pneumatic system 100 for distributing medical objects, such as medicines, according to an embodiment of the present principles. While system 100 is described with reference to distributing medicines 105, system 100 may be configured for distributing various types of medical objects, including but not limited to oral, topical, or suppository pharmaceutical drugs provided in blister packs or small bottles, as well as small medical devices or supplies, such as sterile items, thermometers, bandages, dressings, or the like, used to diagnose, cure, treat, or prevent disease. According to one embodiment, the pneumatic system 100 may be limited to transportation of routine pharmaceutical medications, such as blister packs of acetaminophen, ibuprofen, or the like.

System 100 comprises a sending station 104 connected to one or more receiving stations 102a-n via pneumatic tubing 106. The sending station 104 may be placed at a secure area within the hospital designated as a location from where medicines are distributed to the patients. According to an embodiment, the sending station 104 may be located at the nursing station 110. According to another embodiment, the sending station 104 may be located directly at the pharmacy. After prescriptions for medicines 105 are filled at the pharmacy and sorted at the nursing station 110, they will be placed in the sending station 104 and distributed via pneumatic tubing 106 to the proper receiving station 102a-n in proximity to the patient bedside. Receiving stations 102a-n may be strategically installed in locations throughout a building, such as a hospital, in proximity to the patient's bedside. For example, one or more receiving stations 102a-n may be installed in various locations in proximity to the patient's bedside, including in patient rooms, emergency rooms (ER), operating rooms (OR), phlebotomy rooms, intensive care units (ICU), or other locations where patients are located.

The pneumatic system 100 according to the present embodiments provides for unattended distribution of medicines 105 in a secure environment. Additionally, according to aspects of the present embodiment, system 100 operates without the implementation of any dedicated pneumatic carriers. Instead, medicines 105 are directly transported within the pneumatic tubing 106. Accordingly, immediately after the medicines 105 are received at the nursing station 110, they may be distributed via the sending station 104 to the appropriate receiving station 102a-n where they are stored until administration to the patient. No individual carriers or containers need to get loaded at the sending station 104 or emptied at the receiving stations 102a-n. The medicines 105 may be distributed quickly, safely, and without prolonged handling, effectively eliminating user errors by minimizing extra staff handovers. Additionally, the receiving stations 102a-n at each patient's bedside save the hospital valuable space by providing safe and convenient storage of medicines prior to administration. No medications need to be stored at the nursing station or at the pharmacy. The receiving stations 102a-n also enable the isolation of medicine between patients reducing errors of administering drugs to the wrong patient and improving patient security. The system also relieves hospital personnel and professionals of unnecessary travel by removing duplication of movement by personnel, if for example a nurse has forgotten to bring the medication to the patient's room for administration. Furthermore, the architecture of the pneumatic tube system 100 allows for the creation of a complete chain of custody of a medicine from the pharmacy and/or the nursing station to the patient.

According to some aspects of the embodiments, pneumatic tubing 106 may comprise a flexible reinforced hose. Such a hose may comprise flexible plastic material, such as polyvinyl chloride (PVC), polyethylene, polypropylene, or the like. Although, other materials may also be utilized, including rubber; reinforced or coated fabric, such as polyester, nylon, fiberglass, or the like; silicone; metals such as aluminum alloy, corrugated stainless steel alloy, or the like; or other material known in the art. The hose may comprise a smooth inner surface to prevent the medicines 105 from being caught in the hose. The inner diameter of the hose may range from approximately 1 inch to approximately 4 inches. According to an embodiment, the inner diameter may comprise approximately 2 inches. Accordingly, the hose is large enough to permit the transport of medicines 105 while maintaining small enough inner diameter to reduce the amount of air pressure or vacuum required to efficiently transport the medicines 105 therein. Moreover, the present pneumatic system 100 can be easily installed throughout a hospital due to the flexibility and compact size of the pneumatic tubing 106.

According to some aspects of the embodiments, system 100 may comprise a point-to-point pneumatic system. According to another embodiment, system 100 may comprise a multi-station pneumatic system 100, as shown in FIG. 1, comprising a sending station 104 connected to a plurality of receiving stations 102a-n via a plurality of tubing pathways. Although FIG. 1 demonstrates a one zone pneumatic tube system 100, a system with multiple zones and the inclusion of any number of sending stations 104 and receiving stations 102a-n is possible without deviating from the scope of the present principles. The various pneumatic tubing pathways may be combined or merged via one or more Y-connectors or diverters configured for changing the direction of the tubing pathways.

According to an embodiment, system 100 is a one-way system such that medicines 105 may only travel from the sending station 104 to one of the receiving stations 102a-n in one direction, and not backward. This ensures safety of transmissions and prevents system misuse. System 100 comprises a pump 108 configured for creating pressure differentiation within the pneumatic tubing 106 that facilitates the transmission of medicines 105 from the sending station 104 to the receiving stations 102a-n. Depending on pump location with respect to the sending station 104, pump 108 may either create a positive pressure or a negative pressure within pneumatic tubing 106 to move medicines 105 within the tubing 106. Pump 108 may be configured for generating approximately 4 pounds to approximately 6 pounds of pressure/vacuum. According to one embodiment, pump 108 may comprise a positive pressure air compressor for generating compressed air within pneumatic tubing 106. In such an implementation, for example, the system 100 may comprise a diverter and a single positive air pressure pump or air compressor 108 (as shown in FIG. 3B) in proximity to the sending station 104. Such positive pressure air compressor 108 may be configured to provide positive air pressure to push medicine 105 from the sending station 104 to one of the receiving stations 102a-n via a path created by the diverter. Alternatively, according to an embodiment the pump 108 may comprise a negative pressure compressor or a vacuum pump 108 that creates vacuum within pneumatic tubing 106. In such an implementation, for example, each receiving station 102a-n may comprise a vacuum pump 108 (as shown in FIG. 5B) that pulls the medicine 105 from the sending station 104 to the receiving station 102a-n with negative air pressure. The sending station 104 may comprise multiple inlets each connected via pneumatic tubing 106 to a respective receiving station 102a-n or a diverter creating a path from the sending station 104 to one of the receiving stations 102a-n.

System 100 may further comprise a system controller 112 configured for monitoring and controlling the operation of system 100. The sending station 104, one or more receiving stations 102a-n, a diverter, the pump 108, and other system components, may be connected via a wired or wireless signal communication network 115 with, and controlled by, the system controller 112. Although a single system controller 112 is illustrated, a plurality of system controllers may be utilized. For example, each receiving station 102a-n may comprise a satellite controlling unit. According to another embodiment, the system controller 112 may be integrated within the sending station 104.

In one embodiment, the system controller 112 may comprise at least one central processing unit (CPU). The CPU can represent one or more microprocessors, "general purpose" microprocessors, special purpose microprocessors, application specific integrated circuits (ASICs), or any combination thereof. The CPU can provide processing capability to execute an operating system, run various applications, and/or provide processing for one or more of the techniques and functions described herein. Applications that can run on the system controller 112 can include, for example, software for configuring and operating the pneumatic tube system 100. The system controller 112 may further include a memory communicably coupled to the CPU, which can store data and executable code. The memory can represent any suitable storage medium, such as volatile and/or non-volatile memory, including random-access memory (RAM), read-only memory (ROM), Flash memory, hard disk drive, or the like. In buffering or caching data related to operations of the CPU, the memory can store data associated with applications running on the system controller 112.

The system controller 112 can further comprise one or more interfaces, such as a communication network interface, an analog interface, a wireless network interface, or the like, for connecting to communication network 115. According to an embodiment, the network interface may comprise an Ethernet interface for sending and receiving signals over an Internet Protocol (IP) based network. According to one embodiment, the communication network 115 can provide a wired connection between system components. According to another embodiment, the communication network 115 can comprise a wireless network, such as an IEEE 802.11 based network or Wi-Fi.

The sending station 104, and/or each receiving station 102a-n can comprise a memory and a CPU, such as a microcontroller-based PC board, configured for communicating with and processing various commands and performing operations requested by the system controller 112. The sending station 104 and each receiving station can further comprise a network interface configured for bidirectional communication on the communication network 115 with the system controller 112. The network interface can comprise an analog interface, a communication network interface, a wireless interface, such as a radiofrequency transceiver, or the like.

System controller 112 may communicate with a database 113 for logging various data. The database 113 may be, for example, a relational database, a flat file database, fixed length record database, or any other data storage mechanism known or as yet undiscovered in the art. Further, the database 113 may reside on a stand-alone server, or the same machine as the system controller 112. The database 113 of the pneumatic tube system 100 may store patient files associated with each patient, and preferably with the patient's unique ID accorded to the patient during admission to the hospital. Each patient file may include, for example: a patient ID; name of the patient; room number of the patient; bed number of the patient; receiving station ID associated with the patient; name, strength, diluent, and dosage of drug to be delivered to the patient; and IDs of authorized users allowed access to the receiving station 102a-n associated with the patient. Database 113 may store additional information or less of the above listed information without departing from the scope of the present invention. The system controller 112 uses the above information to properly route medicine 105 from the sending station 104 to a receiving station 102a-n associated with the patient. During delivery the system controller 112 will also keep a log of chain of custody of the medicine 105 based on the information collected before, during, and after transportation.

The system controller 112 may interpret the data in the database 113 and generate commands in the form of signals to individual components in system 100 to control the actions of the system 100. The system controller 112 may control various components of the system 100, such as the pump 108 or a diverter, via relays. In another embodiment, the various components of the system 100, such as sending station 104 and receiving stations 102a-n, may comprise microprocessors configured for interpreting commands received from the system controller 112. The system controller 112 may send commands to pump 108 to activate and thereby create pressure differentiation to transport medicines 105 through the pneumatic tubing 106. The system controller 112 may further generate and transmit commands to the diverters to change position and/or direction of the pneumatic tubing path 106 to route the medicines 105 to the desired receiving station 102a-n via a particular path in the pneumatic transmission tubing 106. In another embodiment, system controller 112 may restrict access to the one or more sending stations 102a-n and provide access only to authorized users as will be described below.

Each sending station 104 and receiving station 102a-n may further comprise an identifying tag reader 116a-n. Furthermore, the pneumatic tubing 106 may include a plurality of inline identifying tag readers 118a-n disposed at various locations along the pneumatic tubing 106. Tag readers 116a-n and 118a-n may be configured for tracking or sensing the medicines 105 as they are transported through the system 100. Tag readers 116a-n and 118a-n may comprise optical sensors, radiofrequency (RF) readers, or the like. Medicines 105 may comprise identification (ID) tags 120 attached or printed on the medicines 105, for example on a label. ID tags 120 may include, but are not limited to optically scannable identifier tag, radio-frequency identification (RFID) tags, near field communication (NFC) tags, barcodes, or similar ID tags that are capable of being read, sensed, or identified by the tag readers 116a-n and 118a-n. Additionally, any other identification technology known, or as yet undiscovered, may be used within the scope of the present principles. Each ID tag 120 may comprise a unique ID number associated with the medicines 105. The tag readers 116a-n at each sending station 104 and receiving stations 102a-n are configured for reading the ID tags 120 attached to the medicines 105 upon departure and arrival, respectively. Optical inline identifying tag readers 118a-n may be implemented for example, through a window in a section of the tubing 106, through an optical sensor disposed in the tubing 106, or the like. Radiofrequency type identifying tag readers 118a-n may be implemented through a radiofrequency antenna disposed on a recess section of the tubing 106. The inline identifying tag readers 118a-n read, or otherwise sense, the passage of medicines 105 comprising an ID tag 120 that is being transported through the pneumatic tube system 100.

In one embodiment of the present principles, each tag reader 116a-n and 118a-n may be used to record information associated with the ID tags 120 attached to the medicines 105 at various locations throughout the pneumatic tube system 100 and send the recorded information to the system controller 112. According to another embodiment, the system 100 may utilize handheld devices 117, such as smartphones or personal digital assistants (PDA), for reading the ID tags 120 and transmitting recorded information to the system controller 112. The recorded information may include the ID number read from the ID tags 120 associated with the medicines 105. The recorded information may also be appended with other relevant information, such as, but not limited to, date and time, location, a unique ID associated with the sending station 104 and receiving station 102a-n, a unique ID associated with the user sending the medicine 105, or other information associated with the transmittal of the medicine 105. The one or more of the appended information may be appended by the tag readers 116a-n and 118a-n, the sending station 104, the receiving station 102a-n, or the system controller 112.

The system controller 112 may receive the recorded information from the tag readers 116a-n at the sending 104 and receiving 102a-n stations, as well as from the inline identifying tag readers 118a-n disposed throughout the pneumatic tube system 100. The system controller 112 may log the recorded information into the database 113. Using the recorded information, the system controller 112 may track each medicine's location throughout the pneumatic tube system 100 as it is sent from the sending station 104, as it moves past inline identifying tag readers 118a-n in the pneumatic tubing 106, and as it is received at the receiving station 102a-n. This creates an auditable trail indicating a chain of custody. The system controller 112 may generate records to show that medicines 105 have been dispatched via the sending station 104, received at a receiving station 102a-n, or passed an inline identifying tag reader 118a-n at a certain time. Location recordation may be used to troubleshoot and initiate error notifications, such as a stuck or lost medicines 105. Additionally, reports on chain of custody of medicines 105 may be generated to keep record of who has dispatched the medicine 105 at the sending station 104, who has received the medicine 105 at which receiving station 102*a-n*, and at which specific point in time.

According to an embodiment, the ID tags 120 may also be associated with destination and intended recipient information configured for allowing automatic identification of an intended receiving station 102*a-n* associated with a patient to whom the medicine 105 is to be delivered. The destination and intended recipient information may include, but not limited to, the patient's name or identification number, a room identification number, a patient's bed identification number, and/or a receiving station identification number. The destination and intended recipient information may be stored in the ID tag 120 or in a patient file on the database 113. The tag reader 116*c* at the sending station 104 may read the ID tags 120 on the medicine 105 and transmit the read information to the system controller 112. The system controller 112 may use the read information to determine the appropriate intended receiving station 102*a-n* associated with the destination and intended recipient information. For example, the ID tag 120 may store the receiving station ID assigned to the patient which is transmitted to the system controller 112 to identify the receiving station. In another example, the system controller 112 receiving the read information may query the patient file stored on the database 113 to identify the receiving station 102*a-n*. For example, the ID tag 120 may store a unique identification number associated with the medicine 105, which is used by the system controller 112 to access the patient file and retrieved correlated receiving station assigned to the patient. After identifying the intended receiving station 102*a-n*, the system controller 112 may generate and transmit commands to the system components, for example to diverters to change position and/or direction of the pneumatic tubing path 106 to route the medicines to the identified receiving station 102*a-n* via a particular path in the pneumatic transmission tubing 106.

According to an embodiment, the information stored and recorded by the system controller 112 may be made accessible to users via a computer 114 in communication with the system controller 112 and/or via a web browser with a remote communication device, such as a desktop computer, a laptop computer, or a handheld electronic device, such as a smartphone. In alternative embodiments, this information may be accessible via stand-alone applications, hard copy documents, or any other useful report format. A user may access the information stored and recorded by the system controller 112 to audit compliance with delivery procedures, to generate compliance reporting and manifest system documentation, to track any missing or problem deliveries, to identify or receiving notifications of system errors, such as when medicines get stuck in pneumatic tubing 106, to manage access rights to the pneumatic system to authorized users, among other tasks.

Referring to FIGS. 2A-2B, there is shown an exemplary embodiment of a pneumatic sending station 200, such as sending station 104, where FIG. 2A illustrates a perspective view of the sending station 200 and FIG. 2B illustrates a partially cross-sectional side view of the sending station 200. The pneumatic sending station 200 is utilized in the pneumatic tube system 100 as an interface to the pneumatic tubing 106 to transport medicines 105 to one of the pneumatic receiving stations 102*a-n*. The sending station 200 may be in signal communication with, and controlled by, the system controller 112 (shown in FIG. 1). The sending station 200 may comprise a housing 202 recessed in a wall 201 within a nursing station, or another location. However, the housing 202 of the sending station 200 may be secured on a wall or to the floor, secured to a counter, attached to a pedestal, or installed via other means within a location. The front face of the housing 202 may include an opening 203 in communication with an opening 204 within the housing 202 connected to pneumatic tubing 106. The opening 204 may comprise a tapered or funnel portion 205 that is wide at the top end and narrow at the bottom end for guiding the medicines 105 into the pneumatic tubing 106. The bottom end of the funnel portion 205 may correspond to the diameter of the pneumatic tubing 106. For example, the top end of the funnel portion 205 may comprise about 3 inches or about 2¼ inches in diameter that will taper down to a bottom end of about 2 inches in diameter.

The opening 204 may further comprise a door 206 configured for closing the top end of the funnel portion 205 to restrict access to the pneumatic tubing 106 so that foreign objects cannot accidentally enter the pneumatic tubing 106. The door 206 may comprise a spring loaded hinge 213 that forces the door 206 shut. The door 206 may comprise a handle 207 that may be pulled by the user to open the door 206. When the handle 207 is released, the spring loaded hinge 213 will force the door 206 to close.

According to an embodiment, sending station 200 may comprise an in-line pump 208. In-line pump 208 may comprise an intake 221 in communication with the funnel portion 205 and an outtake 222 connected to pneumatic tubing 106. The in-line pump 208 may be connected to an air compressor source 218 via an inlet 217 configured for providing compressed air. The in-line pump 208 may be configured for creating a positive pressure at the outtake 222 to transport medicines 105 via pneumatic tubing 106 in one direction from the sending station 200 to an intended receiving station 102*a-n*. This in turn creates a negative pressure at the intake 221 that sucks medicines 105 from the opening 204 toward pump 208. The funnel portion 205 at the sending station 200 may comprise a valve or small opening 212 configured for releasing pressure created by the pump 208 inside the funnel portion 205 such that the user can maintain the door 206 opened.

According to another embodiment, system 100 may contain a plurality of pumps 108 that create negative pressure or vacuum and each located in proximity of a corresponding receiving station 102*a-n* (as will be described and shown with reference to FIG. 5B).

The sending station 200 may further comprise a door open sensor 210 configured for sensing that the door 206 has been opened. According to an embodiment, door open sensor 210 may be a magnetic contact sensor, a proximity sensor, a mechanical limit switch, or the like. The door open sensor 210 may be configured to trigger the pump 208 to activate or turn on. According to an embodiment, the door open sensor 210 may trigger the sending station 200 to send a signal directly to the pump 208 directing the pump 208 to turn on. In another embodiment, the door open sensor 210 may trigger the sending station 200 to send a "door open" signal to the system controller 112 indicating that the door 206 has been opened at the sending station 200. The system controller 112 may then activate the pump 208 via a power transistor and/or relay to route the medicine 105 from the sending station 200 to an intended receiving station 102*a-n*.

According to an embodiment, the system controller 112 may comprise a timer configured for being activated in response to a sensor trigger, such as door open sensor 210 or other sensors described below (e.g., proximity or motion sensor 312). The timer may activate the pump 208 to turn on for a predetermined amount of time sufficient to ensure that contents are delivered to a receiving station 102a-n. According to another embodiment, the pump 108 is activated until the receiving station (e.g., receiving station 500 discussed below) indicates to the system controller 112 that the contents have been received by the receiving station. The receiving station may comprise a proximity or motion sensor (e.g., 521 discussed below) configured for detecting contents within the receiving station. The receiving station may send the sensor trigger to the system controller 112, which in response deactivates the pump 108.

The sending station 200 may contain a touch screen 211 that allows for user input and communication. Touch screen 211 may allow a user to identify the intended receiving station 102a-n and input any other instructions for the handling of the transported medicine 105. In an alternative embodiment, the functions of touch screen 211 may be accomplished using manual buttons, switches or other controls, in which event a screen without touch capability may be used.

According to an embodiment, the sending station 200 may further comprise an identifying tag reader 216 for reading an ID tag 120 attached to the medicines 105. The identifying tag reader 216 may be located in proximity to the narrow bottom end of the funnel portion 205 as shown in FIG. 2B. However, the identifying tag reader 216 can be located in a different location at the sending station 200, for example on a front surface of housing 202 as shown in FIGS. 4A-4B.

In operation, the user may enter information using the touch screen 210, such as the destination information. The destination information may be transmitted to the system controller 112, which may direct any system diverters to create a path to transport the medicine 105 from the sending station 200 to the intended receiving station 102a-n. Then user may then open the door 206 using handle 207. This will cause the door open sensor 210 to trigger, which in turn will cause the pump 208 to activate. Upon receiving the destination information from the user and identifying the intended receiving station 102a-n, the system controller 112 can active the pump 208. The user can then drop the medicine 105 into the opening 204. The medicine 105 is directed using the funnel portion 205 into the pneumatic tubing 106 and substantially immediately transported to the intended receiving station 102a-n via the pressure differentiation created within the pneumatic tubing 106.

Furthermore, in a system using identifying tag readers, the identifying tag reader 216 may sense, scan, or otherwise read the ID tag 120 attached to the medicine 105 and transmit recorded information to the system controller 112. According to an embodiment, the recorded information may comprise a unique ID number associated with the medicine 105 as well as other information described above. The system controller 112 may log that information in the database 113.

Referring to FIGS. 3A-3B, there is shown another exemplary embodiment of a pneumatic sending station 300, such as sending station 104, which automatically identifies and transports the prescribed medicine 105 to the intended receiving station 102a-n. FIG. 3A illustrates a perspective view of the sending station 300 and FIG. 3B illustrates a partially cross-sectional side view of the sending station 300. In this exemplary embodiment, the sending station 300 is shown to comprise a housing 302 mounted to the wall 301. The front face of the housing 302 may include an opening 303 in communication with an opening 304 within the housing 302 connected to pneumatic tubing 106. The opening 304 may comprise a tapered or funnel portion 305, such as funnel portion 205, for guiding the medicine 105 into the pneumatic tubing 106.

In the embodiment shown in FIGS. 3A-3B, the pneumatic sending station 300 comprises a door 306 configured for closing the opening 304. Unlike in FIGS. 2A-2B, the door 306 may open by descending toward the funnel portion 305. The sending station 300 may further comprise a proximity or motion sensor 312 configured for detecting the proximity of a user. Proximity or motion sensor 312 may comprise a passive infrared (PIR) sensor, a microwave sensor, an ultrasonic sensor, a photoelectric sensor, or the like, or any combinations thereof. The door 306 may comprise an automatic door opener 307 configured for automatically opening the door 306. The automatic door opener 307 may comprise an electric motor, a linear actuator, a rotary actuator, an electrical actuator, a pneumatic actuator, a hydraulic actuator, a combustion powered actuator, a mechanical actuator, or a combination thereof.

According to an embodiment, the sending station 300 may further comprise an identifying tag reader 316 for reading an ID tag 120 attached to the medicines 105. The identifying tag reader 316 may be located in proximity to the opening 303 as shown in FIG. 3B. The identifying tag reader 316 may be configured for reading the ID tag 120 and communicating the read information to the system controller 112, which uses that information to route the medicine 105 to a desired receiving station 102a-n. The system controller 112 also logs the read information in the database 113 along with any relevant appended information for tracking purposes.

System 100 may further comprise a pump 308 in proximity to the sending station 300. The sending station 300 may comprise a substantially vertical portion 319 of pneumatic tubing 106 that extends substantially vertically from the funnel portion 305 to a bend 315. The bend 315 may change the direction of the pneumatic tubing 106 from the vertical portion 319 to a horizontal portion 318 of pneumatic tubing 106. The pump 308 may be connected to the pneumatic tubing 106 at the bend 315 in a T configuration and be aligned with the horizontal portion 318. The pump 308 may be a positive pressure air pump, such as a positive displacement air compressor, that directs positive pressure into the horizontal portion 318. Accordingly, when the medicine 105 is received at the funnel portion 305 it is dropped via gravity along the vertical portion 319 towards the bend 315. At the bend 315 the medicine 105 is picked up by the positive pressure to travel along the horizontal portion 318. The horizontal portion 318 may be connected via pneumatic tubing 106 to one or more receiving stations 102a-n.

System 100 may further comprise a diverter 309 in proximity to the sending station 300. The diverter 309 may comprise an inner flexible tube that can travel via rails or robotic arms to align with one of a plurality of outgoing ports to transport medicine 105 to either one of the receiving stations 102a-n. The diverter 309 may be connected to the horizontal portion 318 of the pneumatic tubing 106 opposite to the pump 308.

In operation, initially, when a patient is admitted to the hospital, the hospital assigns the patient a patient ID and one of the receiving stations 102a-n, for example receiving station 102a. The hospital may create an electronic patient file that is stored in database 113. The file may include the patient ID, name of the patient, room number of the patient, bed number of the patient, receiving station ID associated with the patient, and IDs of authorized users allowed access to the receiving station 102a associated with the patient. The information may be dynamic and updated by the hospital staff as required. For example, the IDs of authorized users allowed access to the receiving station 102a may change from time to time depending on the changes of shifts of hospital personnel. Next, the doctor prescribes the medicine 105, for example penicillin, to the patient and the patient file is updated with the drug information, for example, with the name, dosage, strength, and diluent of drug to be delivered to the patient. The prescription is sent to the pharmacy to be filled out.

After the pharmacy fills out the prescription, the medicine container or package is labeled with a unique ID tag 120, which upon scanning retrieves the patient file. The patient file is updated to include the unique ID number associated with the medicine, which is stored in the unique ID tag 120. The medicine 105 is then delivered to the sending station 300. At the sending station 300, the user, such as a pharmacist or a nurse, may place his hand holding the medicine 105 in proximity to the proximity or motion sensor 312 and identifying tag reader 316. Upon detecting proximity or motion of the user, the sensor 312 may trigger the automatic door opener 307 to open the door 306 and the pump 308 to turn on for a predetermined period of time. In a system using a vacuum (i.e., where the pump is located in proximity to the receiving station), the door 307 may be opened via the negative pressure generated by the vacuum 308, without the use of an automatic door opener 307. In yet another embodiment, the funnel portion 305 of the sending station 300 may comprise a proximity or motion sensor configured for detecting the passage of a medicine 105 through the funnel portion 305 and in response to activate the pump 308.

The identifying tag reader 316 at the sending station 300 may sense, scan, or otherwise read the ID tag 120 attached to the medicine 105 and transmit recorded information to the system controller 112. In another embodiment, the sending station 300 may comprise an ID tag, and the sending user may scan or read the ID tag of the sending station 300 and the ID tag 120 attached to the medicine 105 via an identifying tag reader of a handheld device 117, which transmits the recorded information to the system controller 112. Using the unique ID tag 120 of the filled out prescription, the system controller 112 accesses the patient file stored in database 113 and determines the physical destination of the medicine 105. Particularly, the system controller 112 may identify the intended receiving station 102a. Relevant delivery data received from the sending station 300 is logged in the database 113. This data may include the time the medicine 105 was sent, the ID of the sending station 104, the sending user ID, and the ID tag 120 of the medicine 105, as well as other information discussed above.

The system controller 112 sends commands to the components of the pneumatic tube system 100 to route the medicine 105 from the sending station 300 to a particular receiving station 102a associated with the patient. Particularly, the system controller 112 may send a signal to the diverter 309 to change the direction of the tubing pathway to route the medicine 105 from the sending station 300 to the identified receiving station 102a. The user can then drop the medicine 105 into the opening 304, which is directed using the funnel portion 305 into the vertical portion 319 of pneumatic tubing 106. The medicine 105 is dropped via gravity toward the bend 315 and then transported using positive pressure created by the pump 308 to the identified receiving station 102a.

As the medicine 105 is transported within the pneumatic tube system 100, inline tag readers 118a-n scan the ID tag 120 of the medicine 105 and transmit that information to the system controller 112 to be logged as tracking information in database 113.

FIGS. 4A-4B illustrate another exemplary embodiment of a pneumatic sending station 400, such as sending station 104, where FIG. 4A illustrates a perspective view of the sending station 400 and FIG. 4B illustrates a partially cross-sectional side view of the sending station 400. Sending station 400 may comprise a housing 402 including at its front face an opening 403 in communication with an opening 404 within the housing 402 connected to pneumatic tubing 106. The opening 404 may comprise a tapered or funnel portion 405 for guiding the medicine 105 into the pneumatic tubing 106.

The pneumatic sending station 400 may further comprise a door 406 configured for closing the opening 403 on the front face of the housing 402 to restrict access to the pneumatic tubing 106. The door 406 may comprise a spring loaded hinge 408 that forces the door 406 shut. The door 406 may comprise a handle 407 that may be pulled by the user to open the door 406. The door 406 may also comprise a lock 412, such as an electromagnetic lock, that keeps the door 406 closed in place. Other types of locks may also be utilized, such as a key lock.

The front face of the sending station 400 may further comprise a user interface 417 including a keypad for receiving user input. In another embodiment, the user interface 417 may include a touch-screen to receive inputs directly from a user touching the touch-screen. The user interface 417 may be utilized to enter destination as well as security information (e.g., a personal identification number (PIN)) for a user of the sending station 400. The sending station 400 may communicate with the system controller 112 to transmit the destination information for identifying the intended receiving station 102a-n. For example, the user may enter a patient's name associated with receiving station 102a. The system controller 112 receiving the patient's name may identify the receiving station 102a as the intended receiving station.

The sending station 400 may further communicate with the system controller to transmit the user's security information to verify whether the entered PIN belongs to an authorized user. The system controller 112 may query a list of authorized users stored on the database 113 to authenticate the user. Upon successful user authentication, the lock 412 of the door 406 may be released to allow the user to open the door 406 via door handle 407 to access opening 404 to deliver the medicine 105. When the handle 407 is subsequently released, the spring loaded hinge 408 will force the door 406 to close. A successful user authentication, and thereby door unlock, may also trigger the system controller 112 to activate or turn on the pump 108 for a predetermined amount of time, and direct any diverters, to route the medicine 105 from the sending station 400 to the intended receiving station 102a.

In operation, the user may enter the user's ID using the user interface 417. The sending station 400 may communicate the entered user's ID to the system controller 112 for authentication. Upon successful authentication, the system controller 112 may unlock the lock 412 of door 406 and turn on the pump 108. Then user can open the door 406 using handle 407, and drop the medicine 105 into the opening 404. The medicine 105 may be directed using the funnel portion 405 into the pneumatic tubing 106 and substantially immediately transported to the intended receiving station 102a.

According to another embodiment, the front face of the sending station 400 may further comprise an identifying tag reader 416, such as an identifying tag reader 116a-n discussed above. The sending user may scan the ID tag 120 attached to the medicine 105 with the identifying tag reader 416 to determine the intended receiving station 102a and log tracking data, as discussed above. Additionally, an ID tag 421 may be associated with a sending user. The sending users ID tag 421 may be a key fob, a card, a badge, a wristband, or the like. The user ID tag 421 may contain security information, such as a user's personal identification number, for a user of sending station 400. The sending user may scan the sending user ID tag 421, the identifying tag reader 416 may read the user's personal identification number, and the sending station 400 may communicate with the system controller 112 to verify whether the personal identification number belongs to an authorized user. The system controller 112 may query a list of authorized users stored on the database 113 to authenticate a user. Upon successful user authentication, the lock 412 of the door 406 may be released to allow the user to open the door 406 via door handle 407 to access opening 404 to transport the medicine 105. When the handle 407 is subsequently released, the spring loaded hinge 408 will force the door 406 to close. A successful user authentication, and thereby door unlock, may also trigger the system controller 112 to activate or turn on the pump 108 for a predetermined amount of time, and direct any diverters 109, to route the medicine 105 from the sending station 400 to the intended receiving station 102a.

In another embodiment, the sending station 400 may comprise an ID tag, and the sending user may scan or otherwise read the ID tag of the sending station 500, the ID tag 120 of the medicine 105 to be sent, and/or the user ID tag via an identifying tag reader of a handheld device 117, which can send the recorded information to the system controller 112.

In another embodiment, a more passive system may be used for scanning the ID tag 120 attached to the medicine 105 and the user ID tag 421. The identifier tags may be RFID tags which can be read by an RFID identifying tag reader. In such an embodiment, the sending user at the sending station 400 may move near the RFID identifying tag reader 416 while holding the medicine 105, and the reader will read and send the ID information from the sending user and the medicine 105 to the system controller 112. Thus, sending users may advantageously avoid physically scanning each identifier tag. The scanned information from the sending station 400 is transmitted to the system controller 112 where it is stored in the database 113 and interpreted by the system controller 112.

Although each sending station 200, 300, and 400 discussed above is shown with one or more particular types of components and/or configuration, a sending station may include any combination of the components discussed above. For example, the pump configuration shown in FIG. 3B may be applied to sending stations 200 or 400. Alternatively, sending stations 300 and 400 may each comprise an in-line pump 208.

FIGS. 5A-5B illustrate an embodiment of a receiving station 500, such as receiving station 102a-n, where FIG. 5A illustrates a perspective view of the receiving station 500 and FIG. 5B illustrates a partially cross-sectional side view of the receiving station 500. Receiving station 500 may be strategically installed in a location throughout the hospital in proximity to the patient's bedside. The pneumatic receiving station 500 is utilized in the pneumatic tube system 100 as an interface to the pneumatic tubing 106 to receive medicines 105 from a sending station 104. The receiving station 500 may be in signal communication with, and controlled by, the system controller 112 (shown in FIG. 1). According to various embodiments, the receiving station 500 may comprise a housing 501 recessed on a wall 505, or installed secured on a wall or to the floor, secured to a counter, attached to a pedestal, or installed via other means within a location. The front face of the housing 501 may include an opening 503 in communication with an opening 504 through a top face of the housing 501. Opening 504 is configured for mating with a terminal end of pneumatic tubing 106. According to an embodiment, the housing 501 is capable of receiving numerous medicines 105 via multiple deliveries.

The receiving station 500 may comprise a proximity or motion sensor 521 configured for detecting the contents within the receiving station 500. Proximity or motion sensor 521 may comprise a passive infrared (PIR) sensor, a microwave sensor, an ultrasonic sensor, a photoelectric sensor, or the like, or any combinations thereof. The housing 501 may further comprise an indicator light 520, such as a light emitting diode (LED) that is activated upon a trigger by the proximity of motion sensor 521 to indicate that the housing 501 contains a delivery.

The opening 503 on the front face of housing 501 may comprise a door 506 configured for closing the front of the housing 501 to restrict access to the receiving station 500 by unauthorized users. The door 506 may comprise at least one spring loaded hinge 510 that forces the door 506 shut. The door 506 may comprise a handle 507 that may be pulled by the user to open the door 506. When the handle 507 is released, the spring loaded hinge 510 will force the door 506 to close. The door 506 may further comprise a see-through window 511 through which a user, such as a nurse, can observe contents within the receiving station 500. The door 506 may also comprise a lock 512, such as an electromagnetic lock, that keeps the door 506 closed in place. Other types of locks may also be utilized, such as a key lock.

According to an embodiment, system 100 may further comprise a pump 508 in proximity to the receiving station 500. Although, as discussed above, a single pump 508 may be located in the proximity of the sending station 104. The receiving station 500 may comprise a substantially vertical portion 519 of pneumatic tubing 106 that extends substantially vertically from the opening 504 to a bend 515. The bend 515 may change the direction of the pneumatic tubing 106 from the vertical portion 519 to a horizontal portion 518 of pneumatic tubing 106. The horizontal portion 518 may be connected via pneumatic tubing 106 to the sending station 104. The pump 508 may be connected to the pneumatic tubing 106 at the bend 515 in a T configuration and be aligned with the horizontal portion 518. The pump 508 may be a negative pressure air pump, such as a negative displacement air compressor, that directs negative pressure into the horizontal portion 518. Accordingly, the pump 508 may draw the medicine 105 from the sending station 104 towards the pump 508 at the receiving station 500. When the medicine 105 is received at the bend 515, it is dropped via gravity along the vertical portion 519 towards the opening 504 and into the receiving station 500.

According to an embodiment, the receiving station 500 may further comprise an identifying tag reader 516 for reading an ID tag 120 attached to the medicines 105. The identifying tag reader 516 may be located in proximity to the opening 504 in communication with pneumatic tubing 106 as shown in FIG. 5B. The identifying tag reader 516 may be configured for reading the ID tag 120 and communicating the read information to the system controller 112. The system controller 112 may log the read information in the database 113 along with any relevant appended information for tracking purposes.

The front face of the receiving station 500 may further comprise a user interface 502 including a keypad for receiving user input. In another embodiment, the user interface 502 may include a touch-screen to receive inputs directly from a user touching the touch-screen. The user interface 502 may be utilized to enter security information (e.g., a personal identification number (PIN)) for a user of the receiving station 500. The receiving station 500 may communicate with the system controller 112 to transmit the user's security information to verify whether the entered PIN belongs to an authorized user. The system controller 112 may query a list of authorized users stored on the database 113 to authenticate the user. Upon successful user authentication, the lock 512 of the door 506 may be released to allow the user to open the door 506 via door handle 507 to access opening 503 to retrieve the medicine 105. When the handle 507 is subsequently released, the spring loaded hinge 510 will force the door 506 to close.

According to another embodiment, the front face of the receiving station 500 may comprise an identifying tag reader 517, such as an identifying tag reader 116a-n discussed above. The receiving user may scan the ID tag 120 attached to the medicine 105 with the identifying tag reader 517 for tracking purposes. Additionally, an ID tag, such as a key fob 421 discussed above, may be associated with the receiving user containing security information associated with the receiving user. The receiving user may scan the receiving user ID tag, the identifying tag reader 517 may read the user's personal identification number, and the receiving station 500 may communicate with the system controller 112 to verify whether the personal identification number belongs to an authorized user. The system controller 112 may query a list of authorized users stored on the database 113 to authenticate a user. Upon successful user authentication, the lock 512 of the door 506 may be released to allow the user to open the door 506 via door handle 507 to access opening 504 to retrieve the medicine 105.

In another embodiment, a more passive system may be used for scanning the ID tag 120 attached to the medicine 105 and the user ID tag. The identifier tags may be RFID tags which can be read by an RFID identifying tag reader. In such an embodiment, the receiving user at the receiving station 500 may move near the RFID identifying tag reader 516, and the reader will read and send the ID information from the receiving user to the system controller 112 for authentication.

In operation, the medicine 105 may be transported using negative pressure created by the pump 508 through the horizontal portion 518 of pneumatic tubing 106 into the bend 515 and dropped into the receiving station 500 via gravity. As the medicine 105 passes the identifying tag reader 516 at the receiving station 500 the medicine ID tag 120 is automatically scanned to verify delivery. As the medicine 105 is received by the receiving station 500, the proximity of motion sensor 521 may trigger and the visual indicator 520 may light up to notify that the medicine 120 has been received. In another embodiment, the visual indicator 520 may be directed to turn on by the system controller 112 upon receiving delivery information from the identifying tag reader 516. In addition, a notification may be send to a handheld device 117 of the receiving user that the prescription has been received by the receiving station 500.

The medicines 105 may be released from the receiving station 500 by a receiving user when they become due for administering to the patient. The receiving user may be a nurse attending the patient at the bedside of the receiving station 500. The receiving user may unlock the door 506 by entering user ID via keypad 502 or scanning a user ID tag via identifying tag reader 517.

The user identification information may be transmitted to the system controller 112 for authentication and door unlock. The system controller 112 may look up the patient file to determine whether the receiving user is authorized to access the receiving station 500. If so, the system controller 112 sends a command to the receiving station 500 to unlock the door 506. The system controller 112 also logs relevant reception data, including, for example, the contents or medicine ID, the receiving station ID, the time the medicine arrived at the receiving station 500, the time the door 506 has been unlocked, and the receiving user identification information. Then receiving user may then deliver the medicine 105 to the patient. In that step, the receiving user may use a handheld device 117 to scan an ID tag on the patient's wristband or other ID tag located in the proximity of the patient, as well as the ID tag of the prescription to create a log that the prescription has been delivered to the patient.

In another embodiment, the receiving station 500 may comprise an ID tag, and the receiving user may scan the ID tag of the sending station 500, the ID tag 120 of the received medicine 105, and/or the user ID tag via an identifying tag reader of a handheld device 117, which transmits the recorded information to the system controller.

The disclosed embodiments provide a system, software, and a method for automatic and safe distribution of medical objects, such as medicines. It should be understood that this description is not intended to limit the embodiments. On the contrary, the embodiments are intended to cover alternatives, modifications, and equivalents, which are included in the spirit and scope of the embodiments as defined by the appended claims. Further, in the detailed description of the embodiments, numerous specific details are set forth to provide a comprehensive understanding of the claimed embodiments. However, one skilled in the art would understand that various embodiments may be practiced without such specific details.

Although the features and elements of aspects of the embodiments are described being in particular combinations, each feature or element can be used alone, without the other features and elements of the embodiments, or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

The above-described embodiments are intended to be illustrative in all respects, rather than restrictive, of the embodiments. Thus the embodiments are capable of many variations in detailed implementation that can be derived from the description contained herein by a person skilled in the art. No element, act, or instruction used in the description of the present application should be construed as critical or essential to the embodiments unless explicitly described as such. Also, as used herein, the article "a" is intended to include one or more items.

All United States patents and applications, foreign patents, and publications discussed above are hereby incorporated herein by reference in their entireties.

Alternate embodiments may be devised without departing from the spirit or the scope of the different aspects of the embodiments.

What is claimed is:

1. A pneumatic tube system that distributes medical objects in a medical environment without a dedicated carrier, comprising:
   a sending station comprising a housing having a first opening on its front face for receiving a medical object and a second opening in communication with pneumatic tubing for transporting the medical object from the sending station, wherein the second opening comprises a funnel portion that tapers from a wide end to a narrow end, wherein the wide end is in communication with the first opening and wherein the narrow end is in communication with a terminal end of the pneumatic tubing, wherein the funnel portion is configured for guiding the medical object into the pneumatic tubing;
   a plurality of receiving stations routably connected to the sending station via the pneumatic tubing;
   a pump configured for creating a pressure differentiation within the pneumatic tubing for transmitting the medical object from the sending station to one of the receiving stations;
   a system controller in signal communication with the sending station, the receiving station, and the pump, the system controller comprises a processor and a memory encoding one or more processor-executable instructions, which when executed by the processor, cause acts to be performed comprising:
      receiving delivery information from the sending station;
      identifying an intended receiving station using the delivery information; and
      sending commands to the pneumatic tube system to control routing of the medical object from the sending station to the identified receiving station in the pneumatic tubing.

2. The system according to claim 1, wherein the first opening or the second opening comprises a door to restrict access to the sending station.

3. The system according to claim 2, wherein the pump creates a negative pressure proximate to the second opening, wherein the second opening comprises a valve configured for releasing the negative pressure created by the pump proximate to the second opening.

4. The system according to claim 2, wherein the sending station comprises a door open sensor configured for sensing that the door has been opened, wherein the door open sensor is configured for triggering activation of the pump.

5. The system according to claim 2, wherein the sending station comprises a proximity or motion sensor configured for detecting the proximity of a user to trigger at least one of opening of the door and activation of the pump.

6. The system according to claim 2, wherein the door comprises a lock and wherein the sending station comprises a user interface for receiving user identification information to authenticate the user and unlock the door upon successful authentication.

7. The system according to claim 1, wherein the sending station comprises a user interface configured for receiving the delivery information.

8. The system according to claim 1, wherein each receiving station comprises a door to restrict access to the receiving station.

9. The system according to claim 8, wherein the door comprises a lock and wherein the receiving station comprises a user interface for receiving user identification information to authenticate the user and unlock the door upon successful authentication.

10. The system according to claim 1, wherein each receiving station comprises a proximity or motion sensor configured for detecting an arrival of a medical object within the receiving station, wherein the receiving station comprises an indicator light that is activated upon a trigger by the proximity or motion sensor to indicate that the receiving station has received a delivery.

11. The system according to claim 10, wherein notification is send to a handheld device of a user upon a trigger by the proximity or motion sensor to indicate that the receiving station has received the delivery.

12. The system according to claim 1, wherein the system is a one-way system configured for allowing the medical object to travel in one direction from the sending station to one of the receiving stations.

13. The system according to claim 1, wherein the pneumatic tubing comprises a flexible reinforced hose.

14. The system according to claim 13, wherein the hose comprises material selected from the group consisting of plastic, polyvinyl chloride (PVC), polyethylene, polypropylene, rubber, silicone, metal, aluminum alloy, corrugated stainless steel alloy, reinforced or coated fabric, including polyester, nylon, or fiberglass, and any combinations thereof.

15. The system according to claim 13, wherein the hose comprises an inner diameter ranging from approximately one inch to approximately four inches in size.

16. The system according to claim 1, wherein the pump creates one of a positive pressure or a negative pressure within the pneumatic tubing.

17. The system according to claim 1, wherein the pump creates pressure ranging from approximately four pounds to approximately six pounds of pressure.

18. The system according to claim 1, wherein the pump is located in proximity to the sending station and comprises a positive pressure air compressor.

19. The system according to claim 18, wherein the second opening of the sending station is connected to a substantially vertical portion of pneumatic tubing that is connected to a substantially horizontal portion of pneumatic tubing via a bend; wherein the pump is connected at the bend in a T configuration and aligned with the horizontal portion of pneumatic tubing, wherein the medical object is dropped via gravity along the vertical portion until reaching the bend and then travels along the horizontal portion via a positive pressure created by the pump.

20. The system according to claim 19, wherein the horizontal portion of pneumatic tubing is connected to a diverter configured for changing a pneumatic tubing path to route the medical object to the identified receiving station.

21. The system according to claim 1 comprising a plurality of pumps each located in proximity to a respective receiving station and comprises a negative pressure air compressor.

22. The system according to claim 21, wherein the receiving station is connected to a substantially vertical portion of pneumatic tubing that is connected to a substantially horizontal portion of pneumatic tubing via a bend; wherein the pump is connected at the bend in a T configuration and aligned with the horizontal portion of pneumatic tubing, wherein the medical object travels along the horizontal portion via a negative pressure created by the pump until reaching the bend and then dropped via gravity along the vertical portion into the receiving station.

23. The system according to claim 1, wherein the pump comprises an in-line pump connected to a compressed air source configured for creating a positive pressure at an outlet of the in-line pump.

24. The system according to claim 1, wherein at least one of the sending station and receiving station comprises an identifying tag reader configured for reading an ID tag attached to the medical object.

25. The system according to claim 24, wherein the ID tag attached to the medical object comprises delivery information, wherein the identifying tag reader is configured to read the ID tag attached to the medical object to obtain the delivery information, wherein the system controller is configured to interpret the delivery information to identify the intended receiving station.

26. The system according to claim 25, wherein the system controller identifies the intended receiving station by querying a patient file stored on a database with the delivery information, wherein the patient file includes information selected from the group consisting of a unique ID number associated with the medical object, a patient's unique ID, a name of the patient, room ID of the patient, bed ID of the patient, receiving station ID associated with the patient, one or more IDs of authorized users allowed access to the receiving station associated with the patient, name, strength, diluent, and dosage of the medical object and any combinations thereof.

27. The system according to claim 24, wherein the identifying tag reader is configured to read tags consisting of at least one of an optically scannable identifier tag, a barcode, a radio-frequency identification (RFID) tag, a near field communication (NFC) tag, or any combinations thereof.

28. The system according to claim 24, wherein delivery data is logged by the system controller in a database upon scanning the ID tag at the sending station, wherein the delivery data comprises at least one of an ID of the sending station, an ID of the sending user, information obtained from the ID tag, a time and date the medical object was sent by the sending station, and any combinations thereof.

29. The system according to claim 24, wherein reception data is logged by the system controller in a database upon scanning the ID tag at the receiving station, wherein the reception data comprises at least one of an ID of the receiving station, information obtained from the ID tag, a time and date the medical object arrived at the receiving station, the time a door at the receiving station was unlocked and the medical object was retrieved from the receiving station, a receiving user ID, and any combinations thereof.

30. The system according to claim 1 further comprising a diverter comprising a plurality of outlet ports each in communication with a selected receiving station via pneumatic tubing, wherein the diverter is controlled by the system controller to divert the medical object to an outlet port in communication with the identified receiving station.

31. A pneumatic tube system that distributes medical objects in a medical environment without a dedicated carrier, comprising:
  a sending station comprising a housing having a first opening on its front face for receiving a medical object and a second opening in communication with pneumatic tubing for transporting the medical object from the sending station;
  a plurality of receiving stations routably connected to the sending station via the pneumatic tubing;
  a plurality of pumps each located in proximity to a respective receiving station and comprises a negative pressure air compressor for transmitting the medical object from the sending station to the respective receiving station;
  wherein each receiving station is connected to a substantially vertical portion of pneumatic tubing that is connected to a substantially horizontal portion of pneumatic tubing via a bend, wherein a respective pump is connected at the bend in a T configuration and aligned with the horizontal portion of pneumatic tubing, wherein the medical object travels along the horizontal portion via a negative pressure created by the pump until reaching the bend and then dropped via gravity along the vertical portion into the receiving station;
  a system controller in signal communication with the sending station, the receiving station, and the pump, the system controller comprises a processor and a memory encoding one or more processor-executable instructions, which when executed by the processor, cause acts to be performed comprising:
    receiving delivery information from the sending station;
    identifying an intended receiving station using the delivery information; and
    sending commands to the pneumatic tube system to control routing of the medical object from the sending station to the identified receiving station in the pneumatic tubing.

* * * * *